(12) United States Patent
Santangelo et al.

(10) Patent No.: US 12,121,232 B2
(45) Date of Patent: Oct. 22, 2024

(54) TISSUE REPAIR DEVICE AND METHOD

(71) Applicants: Smith & Nephew, Inc., Memphis, TN (US); Smith & Nephew Orthopaedics AG, Zug (CH); Smith & Nephew Asia Pacific Pte. Limited, Singapore (SG)

(72) Inventors: Stephen A. Santangelo, Sturbridge, MA (US); Anthony O'Leary, Walpole, MA (US); Matthew D. Cunningham, Lakeville, MA (US)

(73) Assignees: Smith & Nephew, Inc., Memphis, TN (US); Smith & Nephew Orthopaedics AG, Baar (CH); Smith & Nephew Asia Pacific Pte. Limited, Singapore (SG)

( * ) Notice: Subject to any disclaimer, the term of this patent is extended or adjusted under 35 U.S.C. 154(b) by 273 days.

(21) Appl. No.: 17/949,598

(22) Filed: Sep. 21, 2022

(65) Prior Publication Data

US 2023/0017576 A1 Jan. 19, 2023

Related U.S. Application Data

(62) Division of application No. 16/413,656, filed on May 16, 2019, now Pat. No. 11,484,304.

(Continued)

(51) Int. Cl.
*A61B 17/04* (2006.01)
*A61B 17/00* (2006.01)
(Continued)

(52) U.S. Cl.
CPC ...... *A61B 17/0469* (2013.01); *A61B 17/0401* (2013.01); *A61B 17/06166* (2013.01);
(Continued)

(58) Field of Classification Search
CPC .......... A61B 17/0469; A61B 17/06166; A61B 2017/00367; A61B 2017/00477;
(Continued)

(56) References Cited

U.S. PATENT DOCUMENTS

| 2009/0093679 A1* | 4/2009 | Suigetsu | A61B 1/00128 |
| | | | 600/139 |
| 2010/0130989 A1* | 5/2010 | Bourque | A61B 17/0482 |
| | | | 606/144 |
| 2011/0092988 A1* | 4/2011 | Cohen | A61B 17/0487 |
| | | | 606/151 |

OTHER PUBLICATIONS

Australian Examination Report—Application No. 2019271230 dated Feb. 9, 2024.
(Continued)

*Primary Examiner* — Sarah A Long
*Assistant Examiner* — Raihan R Khandker
(74) *Attorney, Agent, or Firm* — ArentFox Schiff LLP; Joseph M. Maraia; Marlo Schepper Grolnic

(57) ABSTRACT

Embodiments of the invention include a tissue repair system and related components and associated methods that provide for suturing of tissue using three or more suture anchoring implants, including multiple pairs of connected implants in some embodiments, all of which may be deployed from a single device. Some embodiments achieve this by employing a push mechanism capable of being activated to advance the push mechanism incrementally to discrete positions within the device and deploy implants one at a time from the device.

25 Claims, 16 Drawing Sheets

Related U.S. Application Data

(60) Provisional application No. 62/672,795, filed on May 17, 2018.

(51) Int. Cl.
 *A61B 17/06* (2006.01)
 *A61B 90/00* (2016.01)

(52) U.S. Cl.
 CPC .............. *A61B 2017/00004* (2013.01); *A61B 2017/00367* (2013.01); *A61B 2017/00477* (2013.01); *A61B 2017/0053* (2013.01); *A61B 2017/00867* (2013.01); *A61B 2017/0409* (2013.01); *A61B 2017/0422* (2013.01); *A61B 2017/0464* (2013.01); *A61B 2017/047* (2013.01); *A61B 2090/061* (2016.02)

(58) Field of Classification Search
 CPC ...... A61B 2017/0409; A61B 2090/061; A61B 2017/00407
 See application file for complete search history.

(56) References Cited

OTHER PUBLICATIONS

Chinese Search Report—Application No. 201980027046.3 dated Sep. 22, 2023.

* cited by examiner

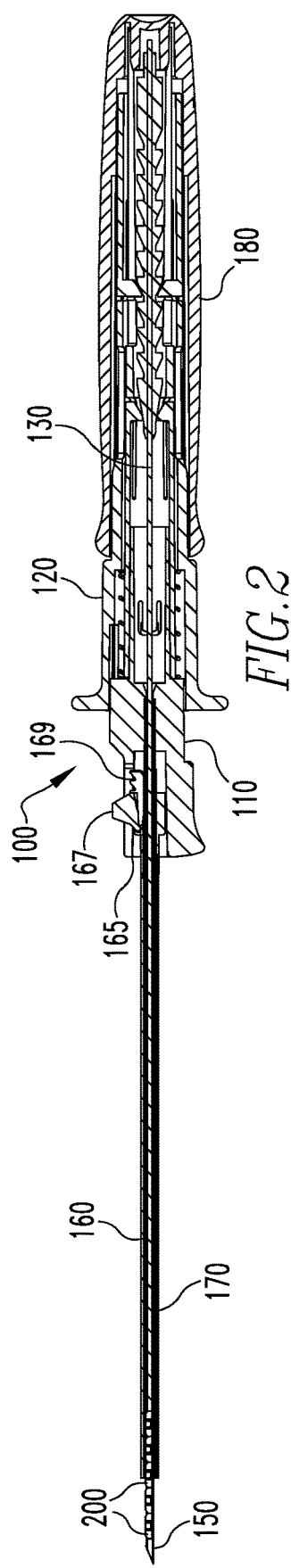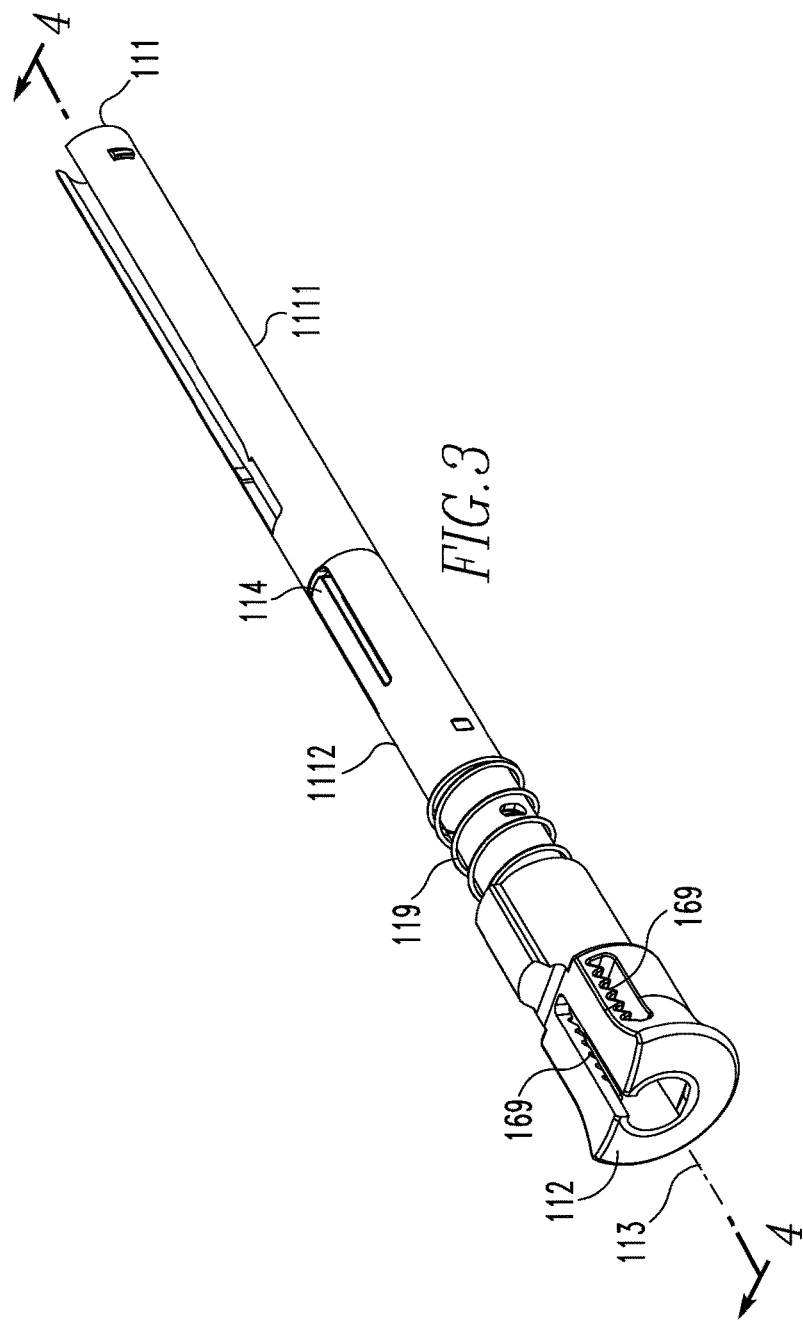
FIG. 2
FIG. 3

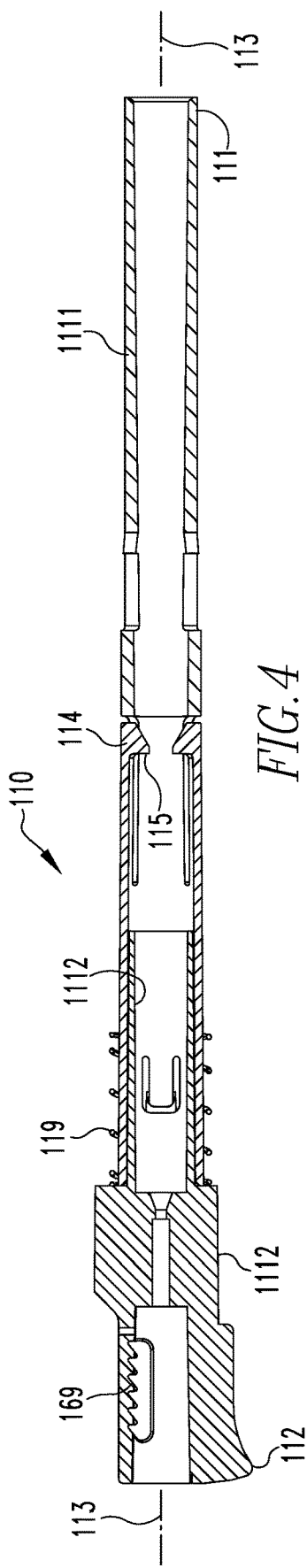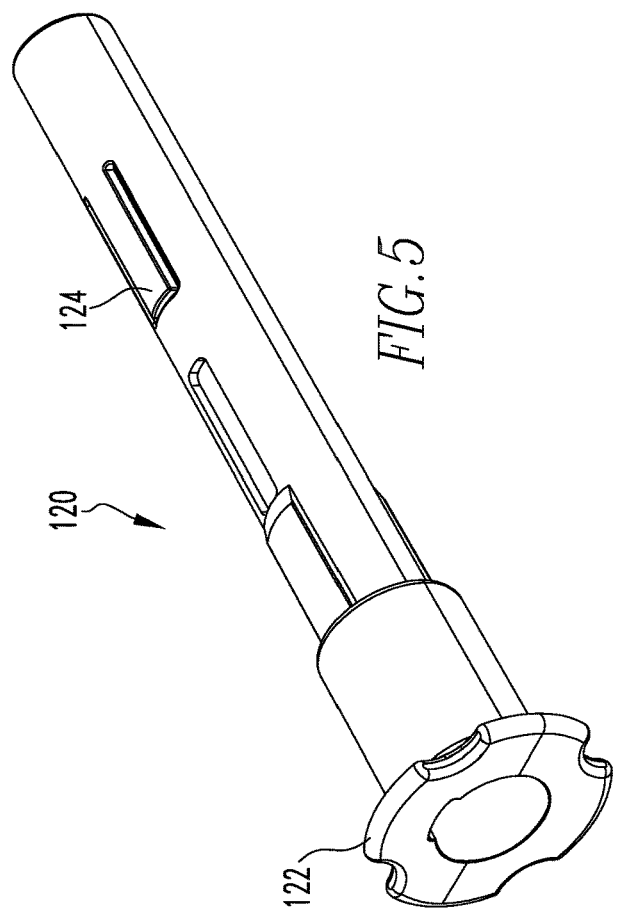
FIG.4
FIG.5

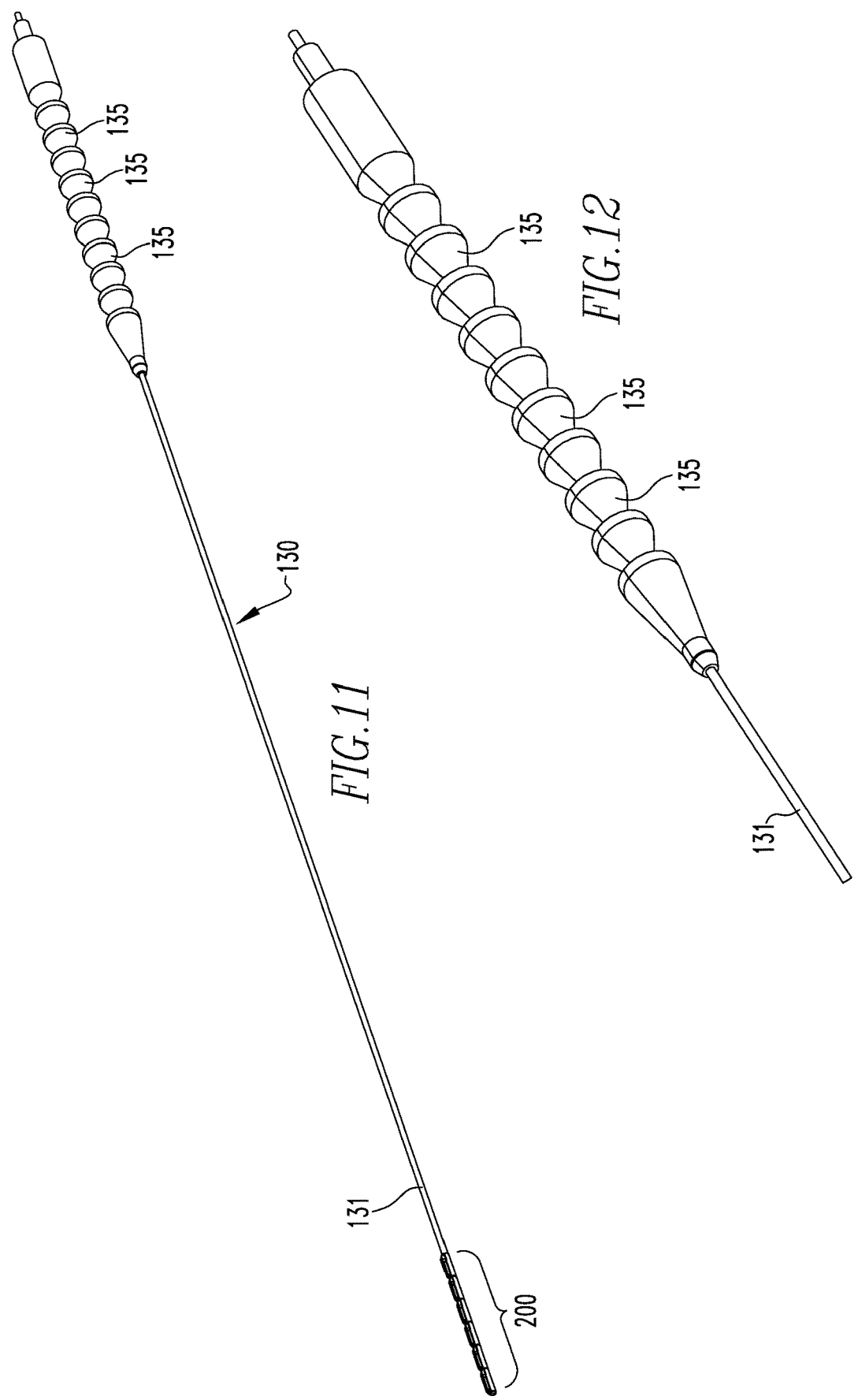

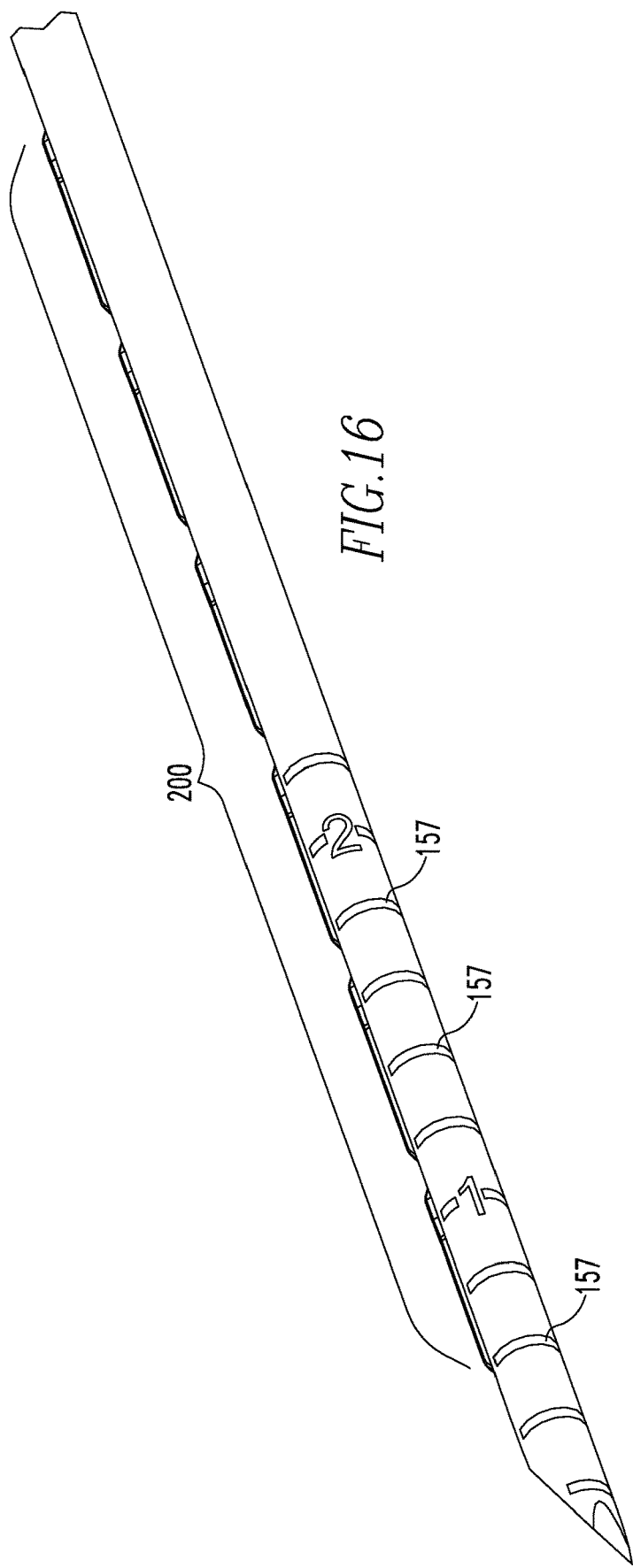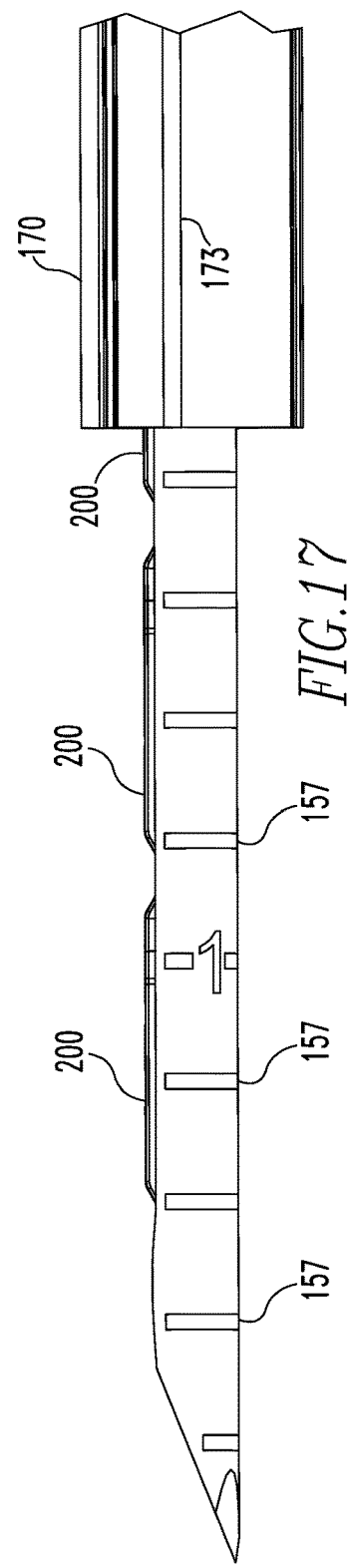

TISSUE REPAIR DEVICE AND METHOD

CROSS-REFERENCE TO RELATED APPLICATIONS

This application is a divisional of co-pending U.S. application Ser. No. 16/413,656, filed May 16, 2019, entitled TISSUE REPAIR DEVICE AND METHOD, which in turn claims priority to and benefit of U.S. Provisional Application No. 62/672,795, filed May 17, 2018, the entire contents of which are incorporated by reference herein for all purposes.

FIELD OF THE INVENTION

The present invention relates generally to the field of tissue suturing instruments and methods, and more particularly relates to a tissue repair system capable of sequentially deploying implants from the same device by activating the instrument repeatedly. Some embodiments are specifically directed to deploying multiple pairs of implants from the same instrument.

BACKGROUND

Tissue repair instruments, such as "All-Inside" meniscal repair instruments currently used, may include an insertion device having a needle containing two deployable larger implants (one set) connected by a knotted suture. Current solutions typically use an implant deployment mechanism that includes one or more push actuation components to individually deploy each implant. Some prior art systems include two separate actuation members that are deployed in a sequential manner to deploy two separate implants. Some prior art systems use a single actuation member that deploys a first implant and is then retracted to be in position to sequentially deploy a second implant.

It would be advantageous to provide a tissue repair system that is capable of sequentially deploying one implant or multiple sets of implants with a single tissue repair device. It would also be an advantage to pre-position singly or multiply grouped implants with pre-attached sutures within the tissue repair device. Improved devices may also be operable to deploy single devices with each discrete cycling on a linear actuator of the tissue repair device. Some improved devices may also include suture management components that separate and protect multiple pre-positioned sutures that may be used with the system. It may also be an advantage to provide implants with smaller diameters and lower profiles than some existing implants. Improved implant may also include anti-rotation features.

SUMMARY

An embodiment of the invention is a tissue repair device that includes a base with a proximal end, a distal end, and a longitudinal axis, a linear actuator movable relative to the base along the longitudinal axis of the base, a push mechanism, and a needle. The push mechanism may be selectively engageable with the linear actuator to be moved distally by the linear actuator relative to the base along the longitudinal axis of the base to at least three discrete positions along the base by reciprocating proximal and distal movement of the linear actuator relative to the base. Each reciprocating proximal and distal movement may engage components of the linear actuator and components of the push mechanism at discrete positions proportional to the at least three discrete positions of the push mechanism along the base. The needle may be coupled to the distal end of the base. A distal portion of the push mechanism may be configured to move distally when the push mechanism is moved distally relative to the base along the longitudinal axis of the base.

Another embodiment of the invention is a tissue repair system with a tissue repair device and a set of implants and sutures. The tissue repair device may include a base with a proximal end, a distal end, and a longitudinal axis, a linear actuator movable relative to the base along the longitudinal axis of the base, and a push mechanism selectively engageable with the linear actuator to be moved distally by the linear actuator relative to the base along the longitudinal axis of the base among discrete positions along the base by reciprocating proximal and distal movement of the linear actuator relative to the base. Each reciprocating proximal and distal movement may engage components of the linear actuator and components of the push mechanism at discrete positions proportional to the discrete positions of the push mechanism along the base. A needle may be coupled to the distal end of the base and a distal portion of push mechanism may move distally through the needle when the push mechanism is moved distally relative to the base along the longitudinal axis of the base. The set of implants and sutures of some embodiments is pre-positioned in the needle and includes two or more pairs of implants for anchoring sutures used to repair tissue, and two or more sutures. The one or more of the sutures may be coupled between one or more respective pairs of the two or more pairs of implants. The coupling of the one or more of the sutures with a pair of implants may include passage of the suture through both implants such that pulling of a proximal free end of the suture tightens a suture length between the implants.

Yet another embodiment of the invention is a method of suturing tissue. The method may include measuring the tissue to be sutured at a first location and setting a depth for a needle of a tissue repair device to penetrate the tissue based on the measurement. A needle may then be inserted through the tissue to be sutured. Method embodiments may also include moving an actuator of the tissue repair device distally relative to other portions of the tissue repair device to engage a push mechanism configured to move a first implant coupled to suture out of a distal end of the needle, and allowing the actuator to move proximally relative to other components of the tissue repair device thereby moving the actuator proximally relative to the push mechanism such that the push mechanism is in position to move another implant from the tissue repair device when the actuator is moved distally again. The implant with coupled suture may then be used to repair tissue.

Still another embodiment of the invention is a method of preparing a tissue repair system to selectively deploy multiple implant sets. The method embodiment may include placing a push mechanism in a base of a tissue repair device, wherein the push mechanism includes multiple teeth along its length that are engageable with a hook of a keeper coupled to the base such that the push mechanism may be moved distally relative to the base, but movement of the push mechanism is limited proximally relative to the base by engagement of the hook with each tooth of the push mechanism. The teeth of the push mechanism may also be engageable with a driver of a linear actuator slideably coupled to the base to move the push mechanism distally when the linear actuator is moved distally relative to the base, but wherein the driver disengages from the teeth to allow proximal movement of the linear actuator relative to the push mechanism. Method embodiments may also include connecting two or more pairs of implants for anchoring sutures with at least one suture per pair of implants, and placing the two or more pairs of implants in a needle capable of penetrating tissue.

BRIEF DESCRIPTION OF THE DRAWINGS

FIG. 2 is a cross-sectional view of the tissue repair system illustrated in FIG. 1, with sutures removed for clarity.

FIG. 3 is a perspective view of a base component of the tissue repair device of the tissue repair system of FIG. 1.

FIG. 4 is a cross-sectional view of the base component illustrated in FIG. 3.

FIG. 5 is perspective view of a linear actuator component of the tissue repair device of the tissue repair system of FIG. 1.

FIG. 11 is a perspective view of the push mechanism and implants of the tissue repair system of FIG. 1.

FIG. 12 is an enlarged perspective view of a proximal end of the push mechanism illustrated in FIG. 11.

FIG. 16 is a bottom perspective view of the distal portion of the tissue repair system illustrated in FIG. 15 showing the needle and implants prior to instrument activation.

FIG. 17 is a side elevation view of a distal portion of the tissue repair system illustrated in FIG. 1 prior to instrument activation and omitting sutures for clarity.

DETAILED DESCRIPTION

Figure 1:
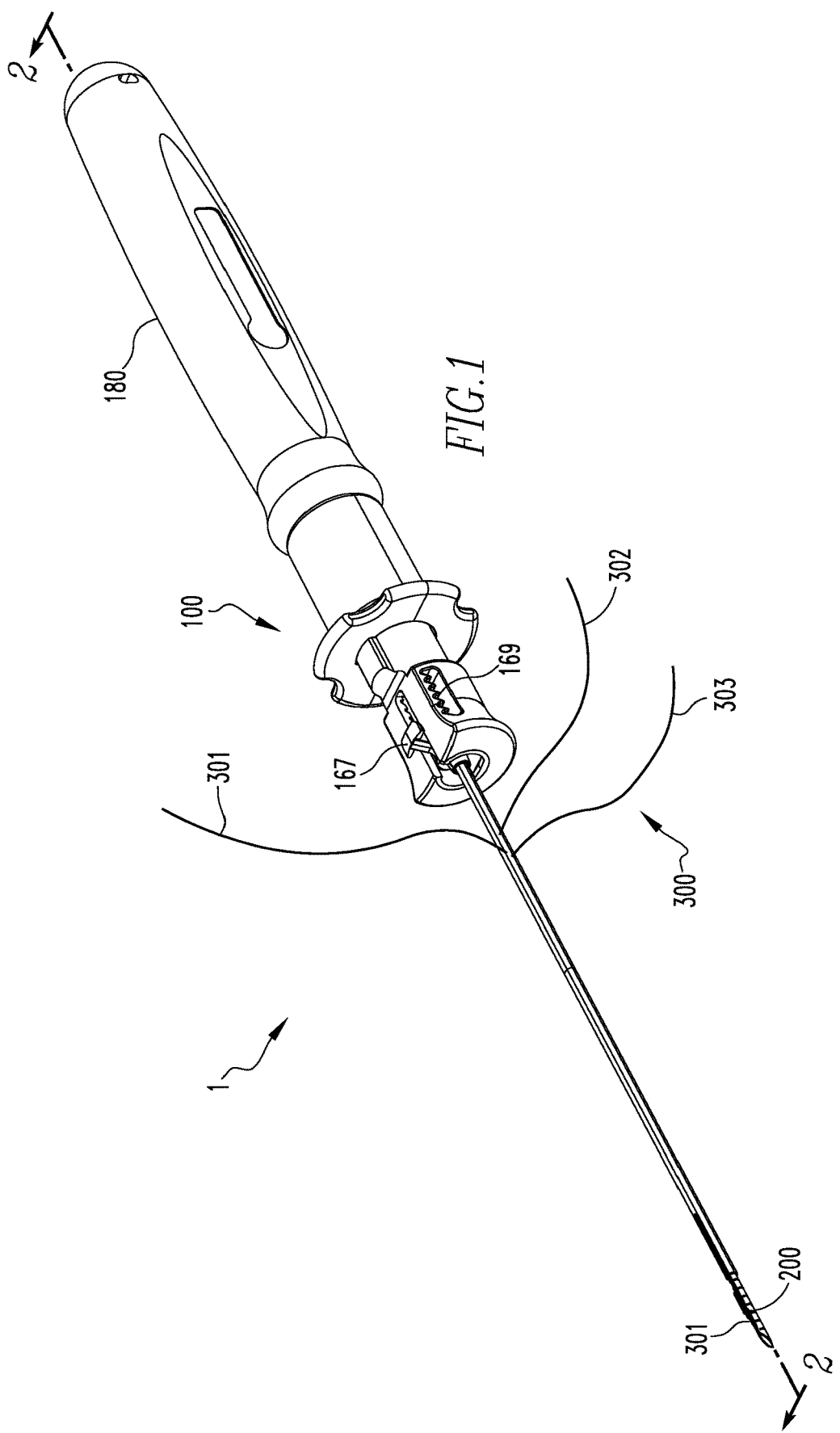
FIG. 1 is a perspective view of a tissue repair system.

An embodiment of the invention is a tissue repair system 1 that includes a tissue repair device 100 and a set of implants 200 and sutures 300 (including sutures 301, 302, 303). The tissue repair device 100 shown in whole or in part in FIGS. 1-23 has a base 110 with a proximal end 111, a distal end 112, and a longitudinal axis 113 (FIGS. 3 and 4). The base 110 depicted is constructed from two components: proximal segment 1111 and distal segment 1112 that are configured to couple together to form the base 110 in the illustrated example. In other embodiments, a base component could be made from a unitary component or in still other embodiments could be further segmented. The base 110 shown in FIGS. 3 and 4 has a keeper 114 with a hook 115, the functions of which will be further described below. The base 110 may also include a handle 180 (FIGS. 1, 2, 6, 7, 13, 18, and 20) fixable near the proximal end 111 of the base 110. The handle 180 may provide a comfortable and ergonomic gripping surface for a user and may provide additional spaces or cavities in which other components of the tissue repair device may reside and operate.

Figure 6:
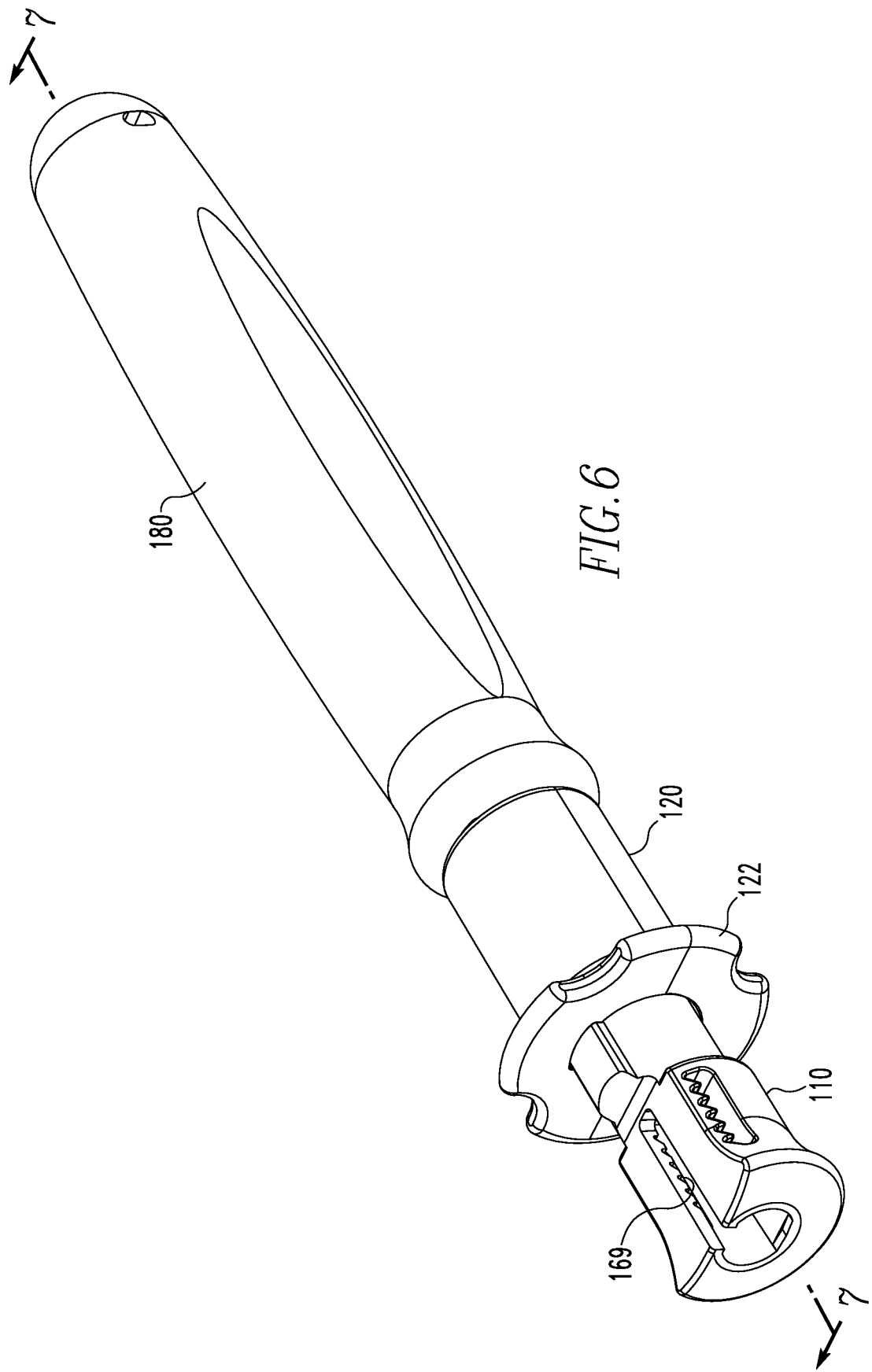
FIG. 6 is a perspective view of the base component, linear actuator, and handle of the tissue repair device of the tissue repair system of FIG. 1.
Figure 7:
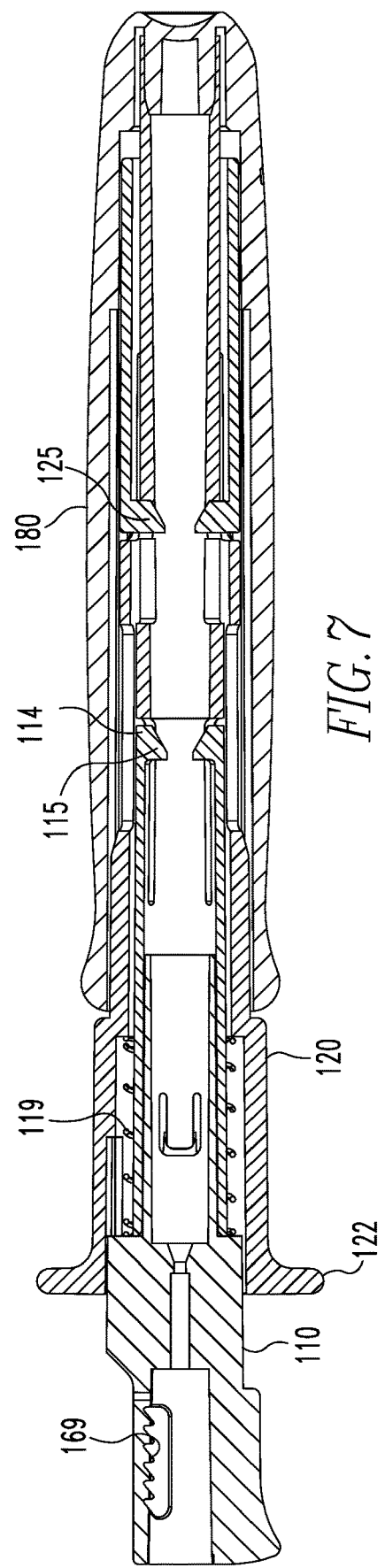
FIG. 7 is a cross-sectional view of the base component, linear actuator, and handle illustrated in FIG. 6.

The illustrated tissue repair device 100 also includes a linear actuator 120 movable relative to the base 110 along the longitudinal axis 113 of the base 110. As shown in FIGS. 5-7, the linear actuator 120 has a flange 122 extending away from a central portion of the linear actuator 120 that is configured to be pushed by a user distally relative to the base 110. In the illustrated embodiment, the linear actuator 120 is spring biased proximally relative to the base 110 by a spring 119 (FIGS. 3, 4, 7, 13, 18, and 20). Other embodiments may be biased by different mechanisms or may require additional user applied force to move a linear actuator proximally relative to a base. In the illustrated embodiment, the linear actuator 120 is movable under the handle 180 in a space between the handle 180 and portions of the base 110, as most easily seen in FIG. 7.

Tissue repair devices of the tissue repair system 1 may also include a push mechanism 130, as illustrated in FIGS. 2, 10-13, 18, and 20. The push mechanism 130 shown is selectively engageable with the linear actuator 120 to be moved distally by the linear actuator 120 relative to the base 110 along the longitudinal axis 113 of the base 110 among discrete positions along the base 110 by reciprocating proximal and distal movement of the linear actuator 120 relative to the base 110. In some embodiments, each reciprocating proximal and distal movement of the linear actuator 120 relative to the base 110 engages components of the linear actuator and components of the push mechanism 130 at discrete positions proportional to the discrete positions of the push mechanism 130 along the base 110. In some embodiments, engagement between a linear actuator and a push mechanism capable of moving the push mechanism may only occur at discrete positions coordinated with the size of implants to be inserted by the tissue repair device. The base 110 shown in FIGS. 3 and 4 includes the keeper 114 and the hook 115 that is located between the base 110 and the push mechanism 130. The keeper 114 and hook 115 collectively allow distal movement of the push mechanism 130 relative to the base 110 but limit proximal movement of the push mechanism 130 relative to the base 110. In the embodiment depicted, this functionality is a result of the keeper 114, which is coupled to the base 110, being configured to flex laterally away from the longitudinal axis 113 of the base 110 to allow distal movement of the push mechanism 130 relative to the base 110. In particular, the sloped distal portions of the teeth 135 of the push mechanism 130 contact the sloped proximal portions of the keeper 114 and displace the keeper 114 laterally away from the longitudinal axis 113 of the base 110 when the push mechanism 130 is moved distally relative to the base 110. However, when the push mechanism 130 is urged proximally relative to the base 110, the hook 115 engages with distal faces of the teeth 135 of the push mechanism 130 to limit proximal movement of the push mechanism 130 relative to the base 110. The resulting movement of this arrangement is ratcheting proximal to distal movement of the push mechanism 130 relative to the base 110. In the illustrated embodiment, the keeper 114 is part of the base 110 and the push mechanism includes teeth 135 for engaging with the keeper 114. In other embodiments, teeth may be located on a base component and a push mechanism may include components configured to engage the teeth and to flex away from the base.

The illustrated tissue repair device 100 includes a needle 150 coupled to the distal end 112 of the base 110 and through which a distal portion of push mechanism 130 moves distally when the push mechanism 130 is moved distally relative to the base 110 along the longitudinal axis 113 of the base 110. As more specifically illustrated in FIGS. 14-17, the needle 150 includes indicia 157 that show a depth from a far distal end of the needle 150 to the indicia 157 to assist a user of the tissue repair device determine depth of penetration of the needle 150 and position of the needle relative to suture management member 170. The needle 150 is depicted as a straight needle and includes a beveled, sharpened end. Other embodiments may include a needle that is curved or that has more than one curved or straight sections. Some embodiments may have a different type of sharpened end or may not be sharpened. The illustrated tissue repair device also includes a sheath 160 in which the some or all of the needle 150 and the implants 200 may be positioned (FIGS. 2 and 8-10).

Figure 10:
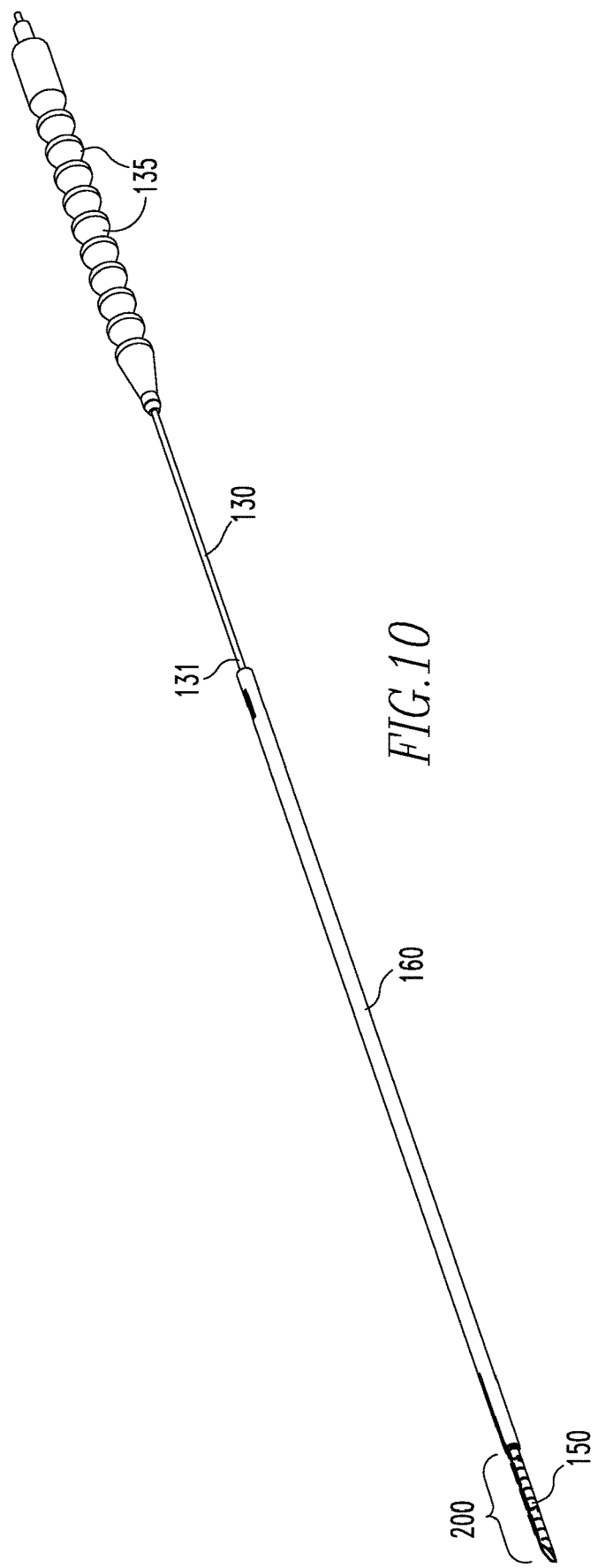
FIG. 10 is a perspective view of the push mechanism, needle, sheath, and implants of the tissue repair system of FIG. 1.
Figure 13:
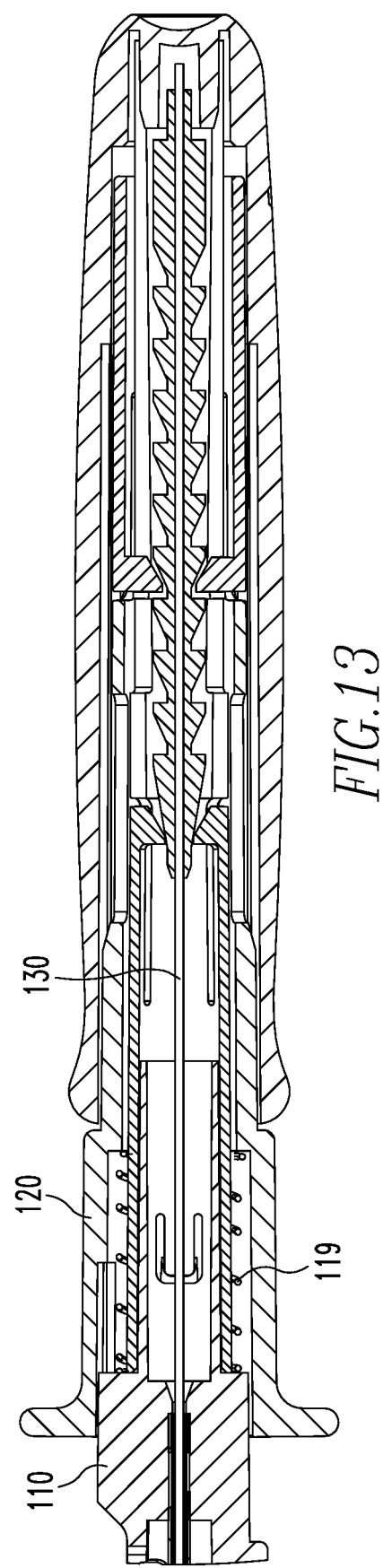
FIG. 13 is a cross-sectional view of a proximal portion of the tissue repair system illustrated in FIG. 1 prior to instrument activation.
Figure 14:
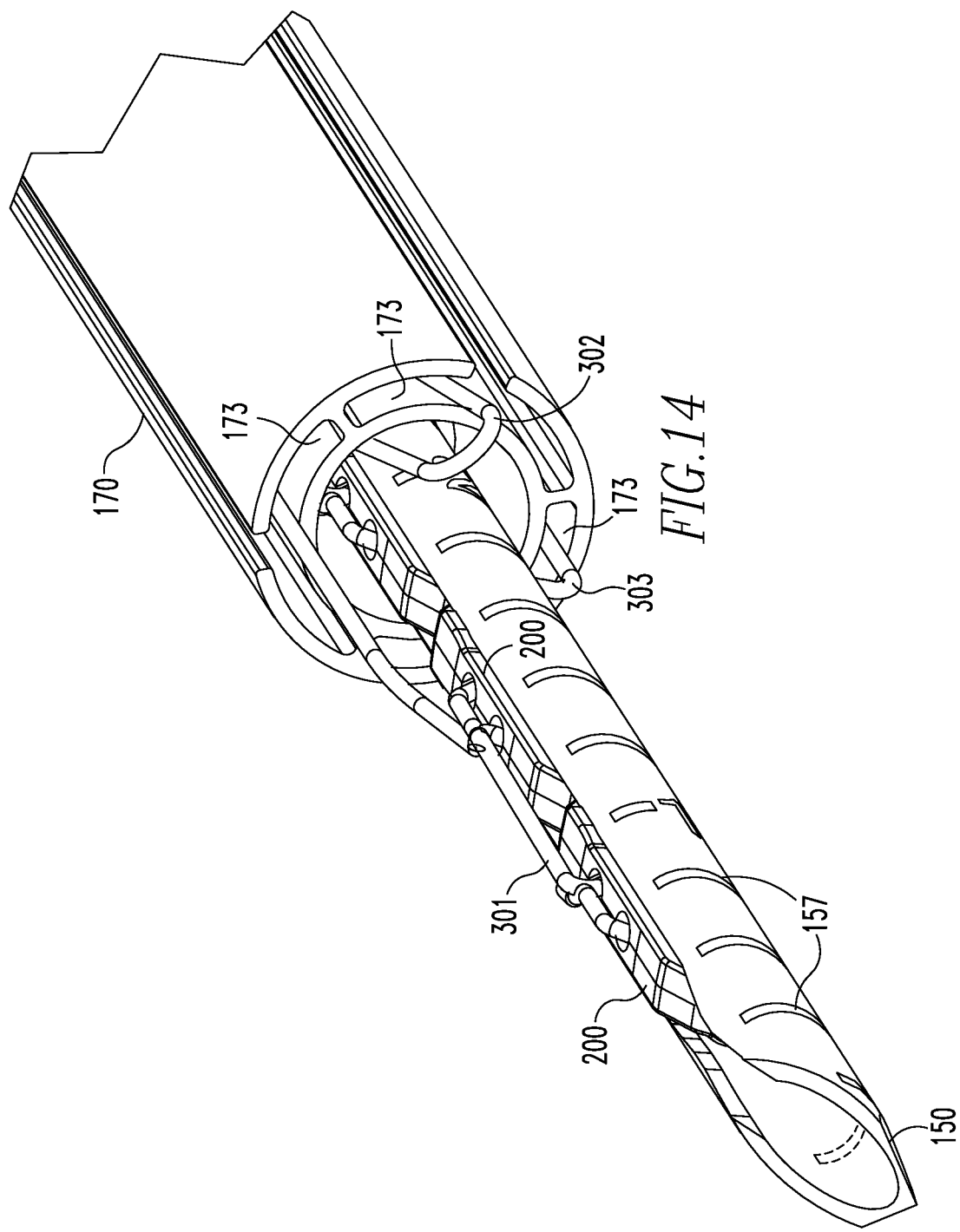
FIG. 14 is a perspective view of a distal portion of the tissue repair system illustrated in FIG. 1 prior to instrument activation.

As shown most clearly in FIGS. 10-12, the push mechanism 130 includes a push rod 131 at its distal end sized to pass into the needle 150 and contact an implant of the implant set 200 for anchoring sutures 301, 302, 303. In the embodiment shown, the push rod 131 extends along most of the length of the tissue repair device 100 and is also a central support shaft for the teeth 135. The teeth 135 shown are near a proximal end of the push mechanism 130 and have spacings that correlate with the discrete positions of the push mechanism 130 along or relative to the base 110. The teeth 135 of the illustrated embodiment are also configured to be engaged by a driver 125 of the linear actuator 120. Some embodiments may include a keeper but not a driver engageable with the teeth, others may have a driver but not a keeper engageable with the teeth, and others, as is the case with the illustrated embodiment, may have a driver and a keeper that are engageable with the same set of teeth. Each of the illustrated teeth 135 include frusto-conical portions, have a flat proximal end, and are located sequentially along the central support shaft (push rod 131) of the push mechanism 130.

The driver 125 of the linear actuator 120 is configured to flex laterally to allow proximal movement of the driver 125 relative to the push mechanism 130 when the linear actuator 120 moves proximally relative to the base 110. Additionally, the driver 125 engages with the teeth 135 of the push mechanism 130 to move the push mechanism 130 distally when the linear actuator 120 is moved distally relative to the base 110. In this way, the push mechanism 130 is selectively engageable with the linear actuator 120 to be moved distally by the linear actuator 120 relative to the base 110 along the longitudinal axis 113 of the base 110 to at least three discrete positions along the base 110 by reciprocating proximal and distal movement of the linear actuator 120 relative to the base 110. The push mechanism 130 includes ten flat proximal ends of teeth 135, seven of which may be engaged by the driver 125, which in the illustrated embodiment defines seven discrete position possibilities along the base 110.

The tissue repair device 100 depicted also includes a suture management member 170 (FIGS. 2, 8, 9, 14, 17, 19, and 21) with more than two separate areas 173 for respectively attaching in each area one or more sutures that may be used with implants or for stitching when performing a surgical procedure with the tissue repair device 100. The suture management member 170 is a double walled tube with slots along the outer wall through with sutures may be passed. Other embodiments may include other structures that form separate areas in or along a suture management member.

Figure 8:
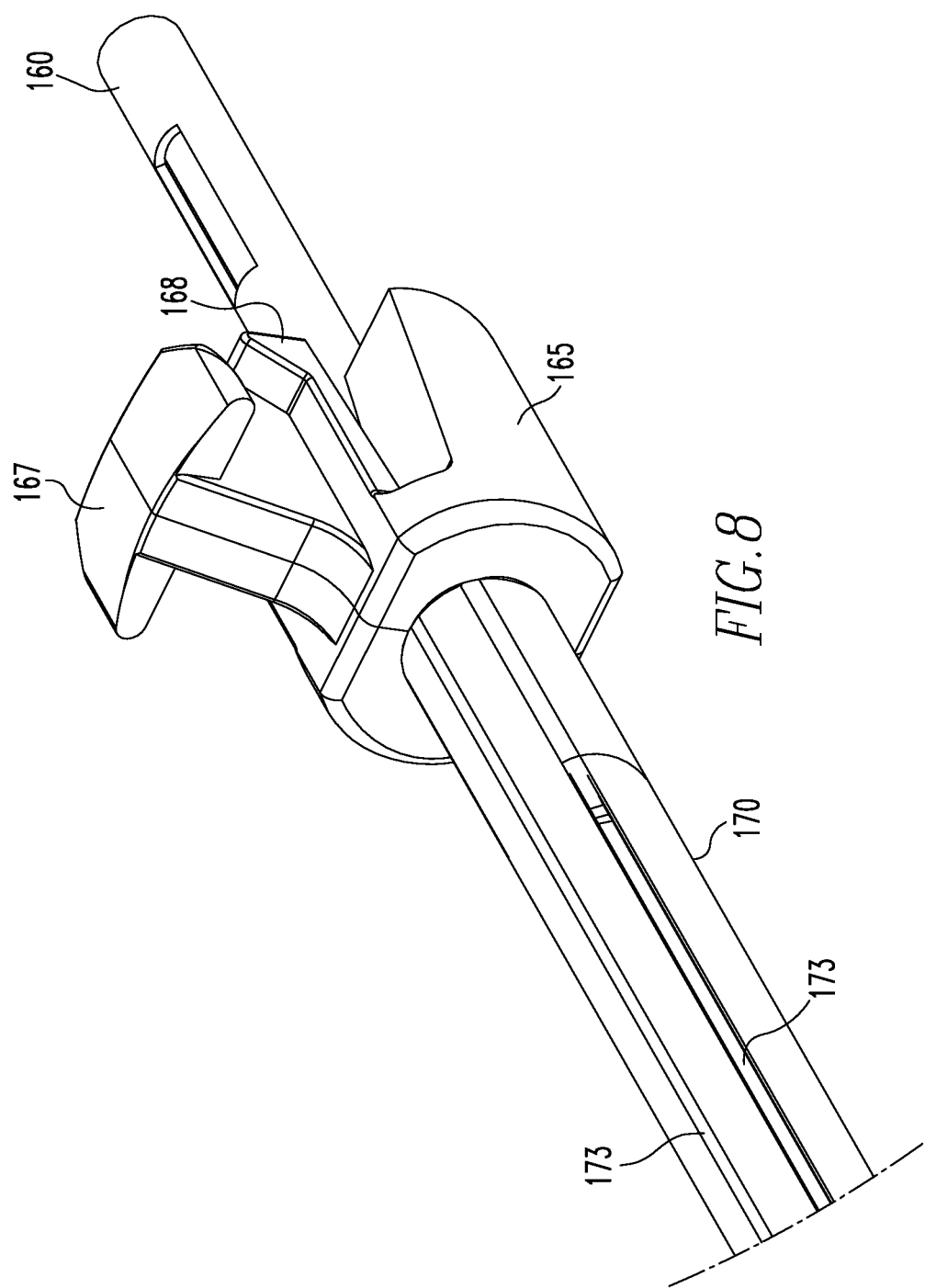
FIG. 8 is a perspective view of a depth adjustment mechanism and other central-distal components of the tissue repair device of the tissue repair system of FIG. 1.

The tissue repair device 100 may also include a depth tube coupled to the base by a depth adjustment mechanism 165, as shown in FIG. 8. In this embodiment, the depth tube is also the suture management member 170, but in other embodiments may be a separate tube. The depth adjustment mechanism 165 is configured to selectively allow a distal end of the depth tube (suture management member 170) to be positioned closer to and farther from the distal end 112 of the base 110. In this embodiment, the depth tube (suture management member 170) depicted is coupled near its proximal end (FIG. 2) to the base 110 by a depth adjustment mechanism 165 (FIGS. 2 and 8) configured to selectively allow a distal end of the depth tube (suture management member 170) to be positioned closer to and farther from the distal end 113 of the base 110. For example and without limitation, the depth tube (suture management member 170) of some embodiments is adjustable along an adjustment distance of 10-20 mm. Other embodiments may include more or less adjustment depending on the size of tissue to be penetrated by a needle of the respective suture passer and the potential variability of the tissue to be penetrated by the needle. When the needle 150 is fixed relative to the distal end 113 of the base 110, adjustment of the depth tube (suture management member 170) relative to the distal end 113 of the base 100 is equivalent to adjustment of the depth tube (suture management member 170) relative to the needle 150. Embodiments of the tissue repair device 100 may include a release 167 (FIGS. 1, 2, and 8) to disengage and engage a catch 168 (FIG. 8) between the base 110 and the depth tube (suture management member 170). In the illustrated embodiment, the release 167 is coupled with the depth tube (suture management member 170) and the catch 168 interacts with notches 169 (FIGS. 1-4, 6, and 7). The release 167 shown is a spring biased button, but in other embodiments may be any effective mechanism, such as but not limited to, a knob, a set screw, or a pin. The notches 169 of the illustrated embodiment are a set distances apart along a longitudinal axis of the tissue repair device 100. The release 167 is coupled to the depth tube (suture management member 170) and is engageable in the notches 169 to guide adjustment of the depth tube (suture management member 170) relative to the base 110 at the set distances. Adjustment may include holding adjustment at specific places. The notches 169 may be at set distances along the base 110, such as, by way of nonlimiting example, 2 mm center-to-center. Some embodiments may include continuous adjustment, for example, along a thread, and relative position may be determined by observation.

In the illustrated embodiment, the needle 150 is substantially concentric in the depth tube (suture management member 170) along a majority of the length of the depth tube (suture management member 170) and is rigid relative to the depth tube (suture management member 170). In other embodiments, a needle may be offset within a depth tube. A depth tube of some embodiments may be flexible to a similar or even greater degree compared with a needle.

Figure 9:
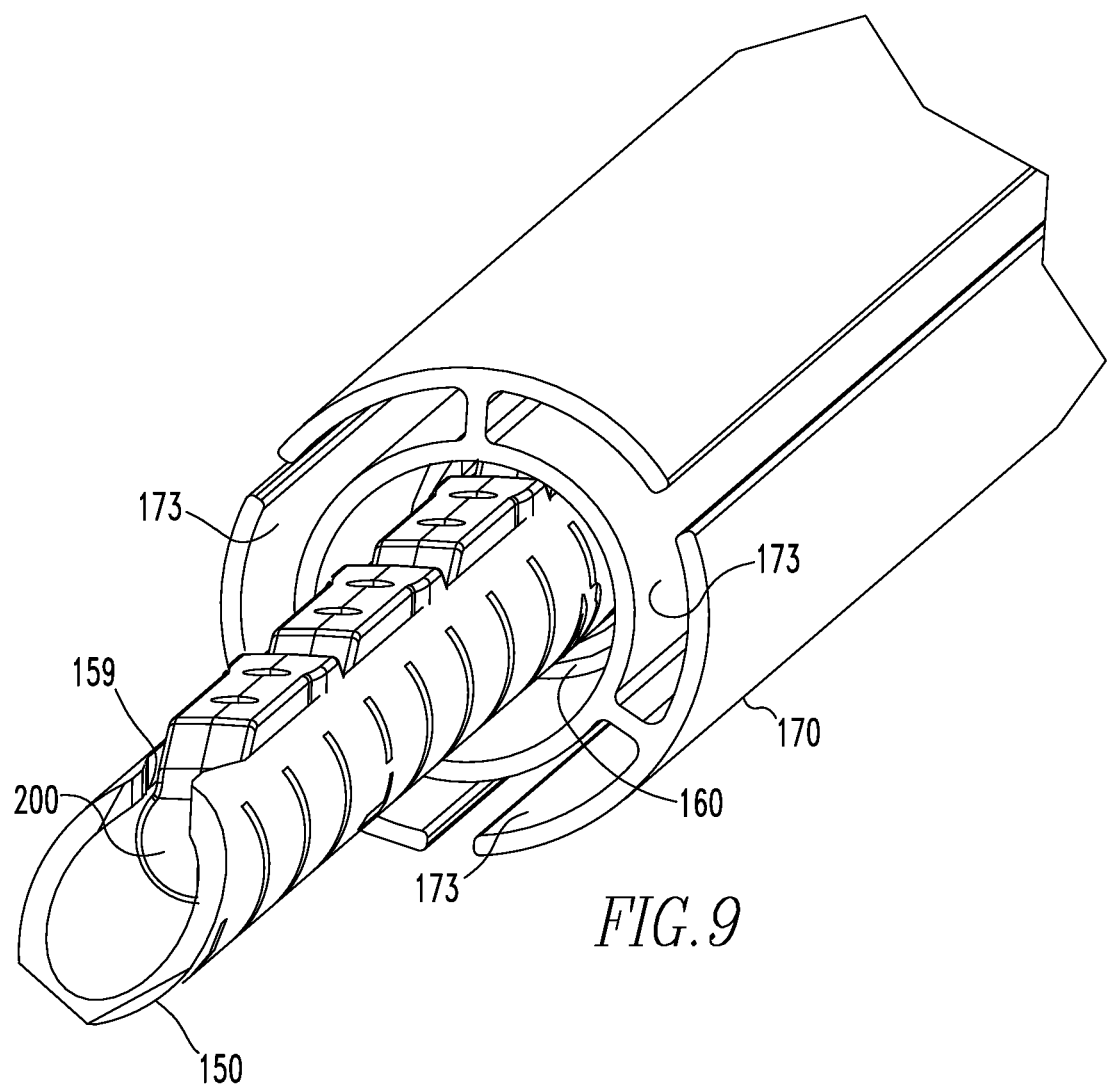
FIG. 9 is a perspective view of the tissue repair system of FIG. 1 from a far distal perspective, with sutures removed for clarity.
Figure 15:
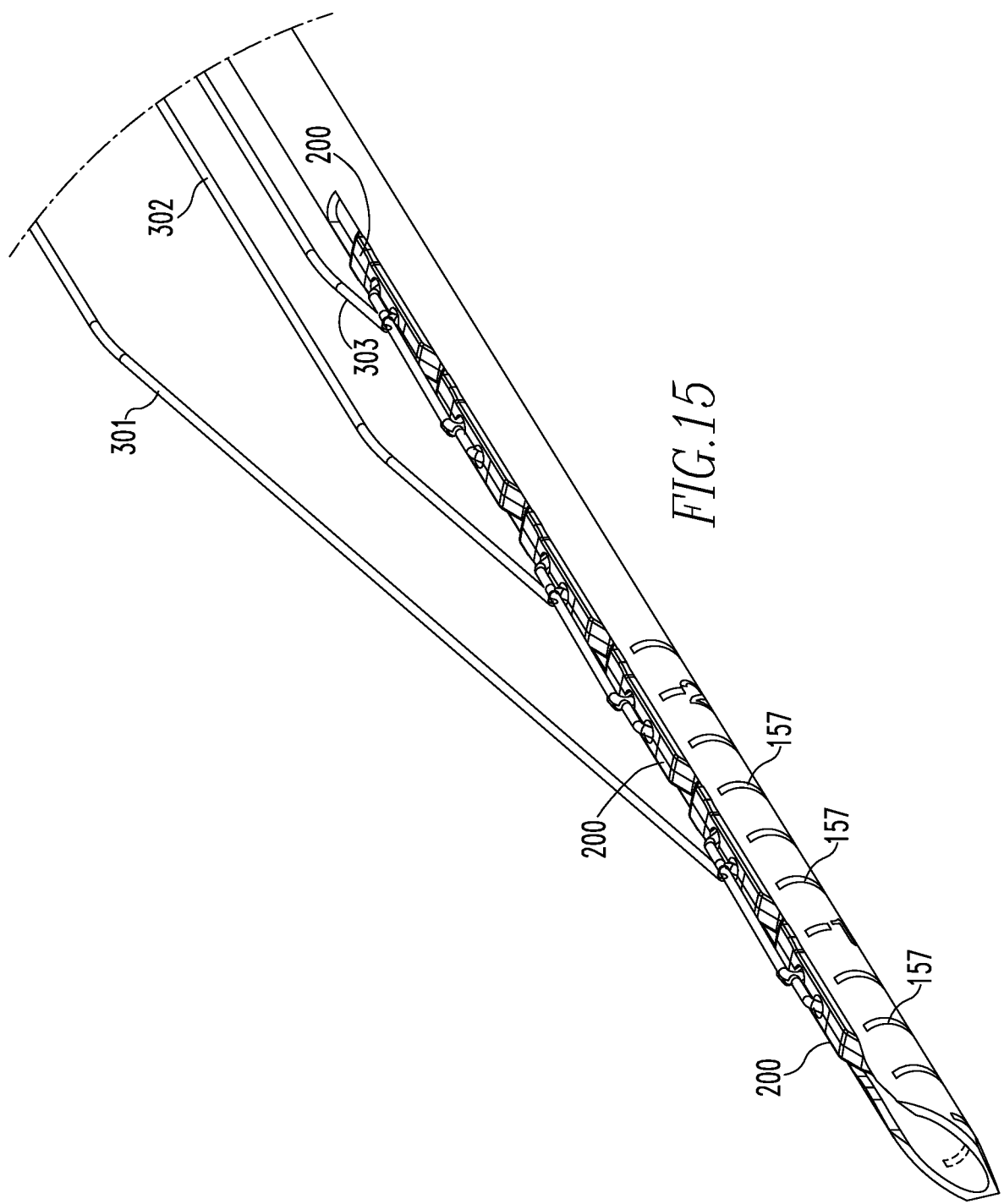
FIG. 15 is a perspective view of a distal portion of the tissue repair system illustrated in FIG. 1 showing the needle and implants with sutures prior to instrument activation.
Figure 21:
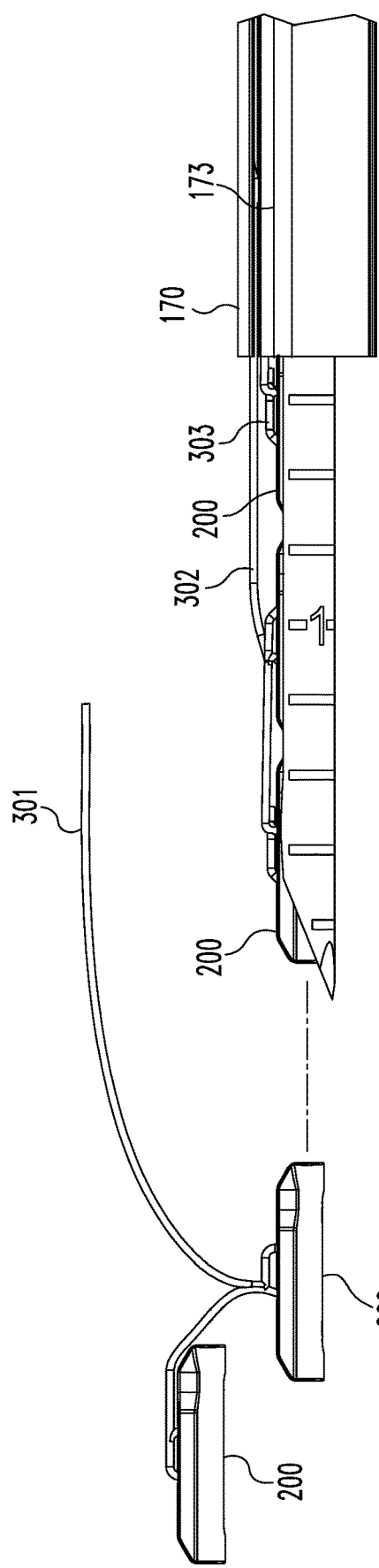
FIG. 21 is a side elevation of the distal portion of the tissue repair system illustrated in FIG. 1 after additional instrument activation, and including illustration of the sutures.
Figure 22:
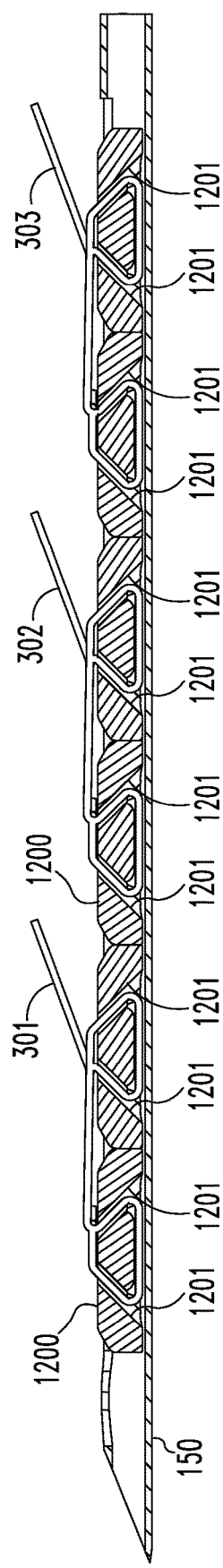
FIG. 22 is a cross-sectional view of a needle and alternate implants with sutures.
Figure 23:
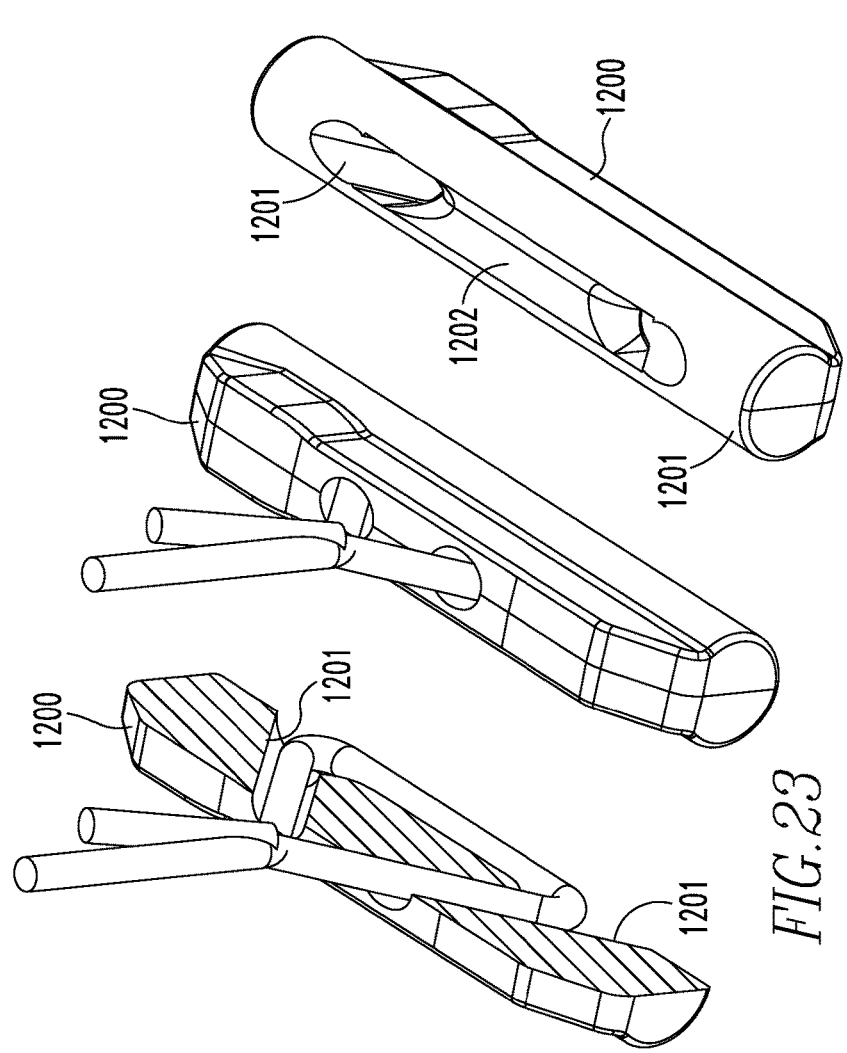
FIG. 23 is a perspective view of the alternate implant and suture illustrated in FIG. 22 showing a cross-section, a side-top, and a side-bottom.

The tissue repair system 1 illustrated also includes a set of implants 200 (FIGS. 1, 2, 9-11, 14-17, 19, and 21) and sutures 301, 302, 303 (FIGS. 1, 14, 15, and 21) pre-positioned in the needle 150. As most clearly visualized in FIG. 15, two or more of the implants 200 may be paired together and coupled with a common suture 301, 302, 303 that may be used to repair tissue. For example and without limitation, tissue may be bound together by the sutures 301, 302, 303 between respective implants or implant pairs 200 after insertion of the implants where desired. Tissue repairs may also include tightening of the sutures 301, 302, 303 between respective implants or implant pairs 200. In particular, the coupling of one or more sutures with a pair of implants may include passage of one or more sutures through both implants of a pair of implants such that pulling of a proximal free end of the suture tightens a length or loop of suture made between the implants. Three pairs of implants 200 are illustrated in FIG. 15, but other embodiments may include fewer or more pairs of implants or one or more single implants configured for deployment from a tissue repair device. An alternate embodiment of an implant suitable for use in some embodiments of the invention is illustrated in FIGS. 22 and 23 by implants 1200 in combination with sutures 301, 302, 303. Holes 1201 in the implants 1200 are sloped to allow for easier sliding of the sutures 301, 302, 303 within the implants 1200. Additionally, each of the implants 1200 may include a scallop 1202 on its bottom (third view in FIG. 23, with suture removed for clarity) in which a suture 301, 302, 303 may be recessed to reduce the overall profile of the implant and suture constructs. The implants 200, 1200 are configured to slide in an anti-rotation slit 159 in the needle 150 (FIG. 9). However, the implants 200, 1200 have a reduced-profile portion of material configured to fit within the anti-rotation slit 159, thereby reducing the overall profile of the needle 150 and implant 200 combined construct.

Figure 18:
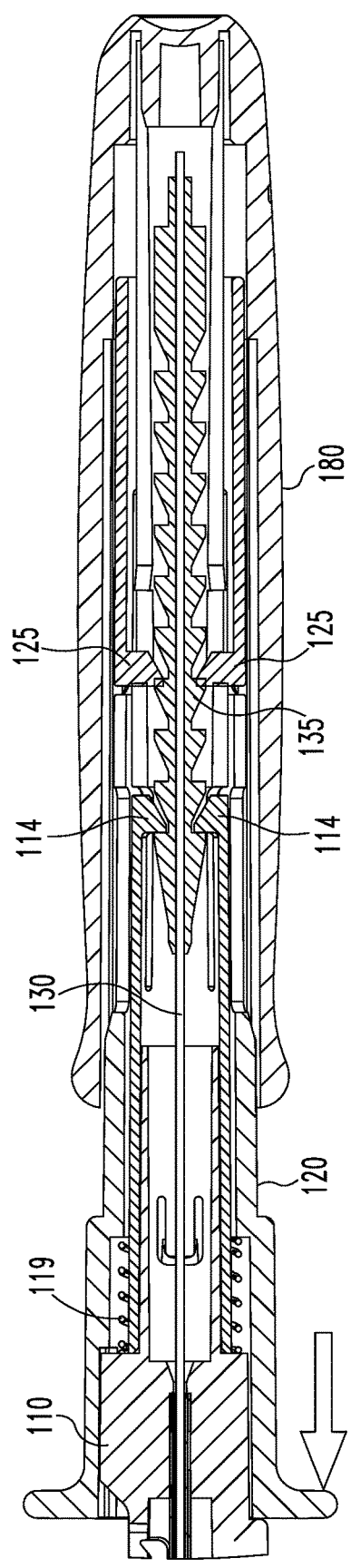
FIG. 18 is a cross-sectional view of the proximal portion of the tissue repair system illustrated in FIG. 13 after instrument activation, as indicated by the action arrow.
Figure 19:
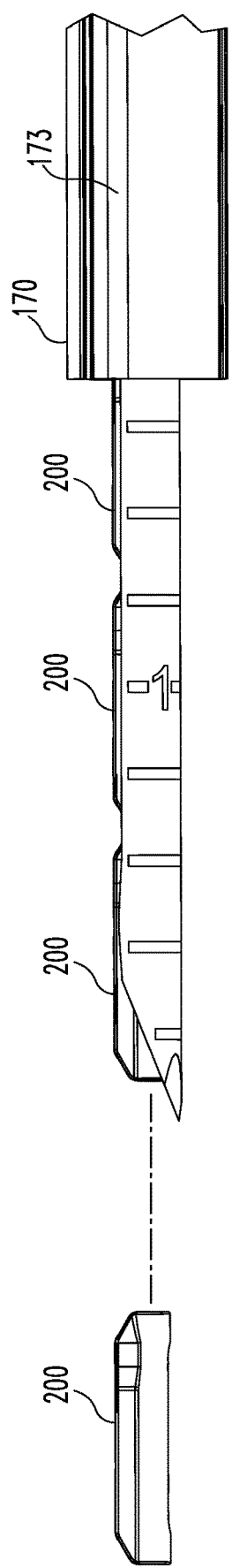
FIG. 19 is a side elevation of the distal portion of the tissue repair system illustrated in FIG. 1 after instrument activation as illustrated in FIG. 18 and omitting sutures for clarity.

An embodiment of the invention is a method of suturing tissue. Example acts of the method embodiment are illustrated in FIGS. 17-21. A side elevation view of a distal portion of the tissue repair system 1 is illustrated in FIG. 17 prior to tissue repair device 100 activation and omitting sutures for clarity. While in this configuration, method embodiment may include measuring the tissue to be sutured and setting the depth tube (suture management member 170) with the depth adjustment mechanism 165 while observing the indicia 157. With a desired depth set, acts of the method may include inserting the needle 150 through the tissue to be sutured and move the linear actuator 120 distally relative to the handle 180 and base 110 as shown by the action arrow in FIG. 18. The proximal portion of the tissue repair device 100 is illustrated in FIG. 18 after instrument activation, and the distal end of the tissue repair device is shown in FIG. 19. Sutures are omitted for clarity. During activation, the driver 125 is engaged with teeth 135 of the push mechanism 130 to move the push mechanism distally with the linear actuator 120. The keeper 114 components are configured to be pushed laterally during activation and retract into engagement with the most distal tooth of the teeth 135. The spring 119 is compressed between the base 110 and the linear actuator 120 to generate a biasing force. The most distal implant 200 is shown in FIG. 19 to be separated from the needle 150 of the tissue repair device 100.

Figure 20:
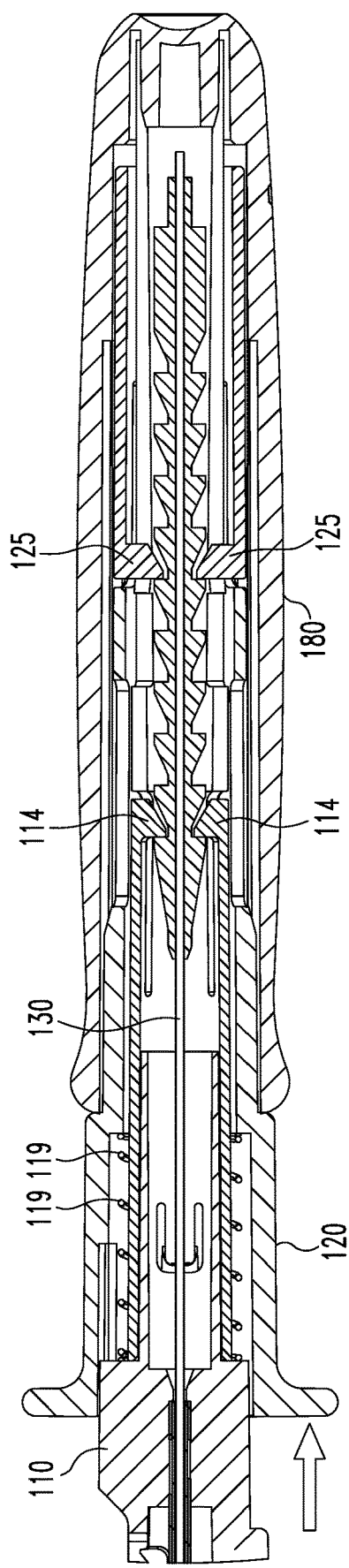
FIG. 20 is a cross-sectional view of the proximal portion of the tissue repair system illustrated in FIG. 13 after additional instrument activation caused by response of a spring force between the base and the linear actuator, as indicated by the action arrow, thereby completing a full cycle of instrument activation.

Deployment of the most distal implant 200 from the distal end of the push rod 131 of the push mechanism 130 results from pushing against the set of implants 200 and moving the implants 200 relative to the needle 150. When a user releases distally directed force from the linear actuator, the linear actuator 120 will move in the direction of the action arrow in FIG. 20 to result in a cycling of the instrument as shown in FIG. 20. More specifically, the keeper 114 will prevent the push mechanism 130 from moving proximally relative to the base 110 and the driver 125 will be pushed laterally to allow linear actuator 120 to move proximally relative to the push mechanism 130. The tissue repair device 100 is then configured to be cycled again to eject another implant 200.

Another act of a method embodiment may include measuring the tissue to be sutured at a location of a next suture and setting the depth tube (suture management member 170) with the depth adjustment mechanism 165 while observing the indicia 157. With a desired depth set, the method may include inserting the needle 150 through the tissue to be sutured and moving the linear actuator 120 distally relative to the handle 180 and base 110 as shown by the action arrow in FIG. 18. The result of another cycling of the tissue repair device 100 (deployment of a second implant 200) is illustrated in FIG. 21, and includes an illustration of the sutures 301, 302, 302.

An additional act of a method embodiment may include pulling a proximal free end of the suture 301 to tighten a loop or length of suture 301 made between the two most distal implants 200. The acts of the method described above may be repeated to deploy each of the pairs of implants 200 and respective sutures 302, 303.

Another embodiment of the invention is a method of preparing a tissue repair system to selectively deploy multiple implant sets. Acts of such an embodiment may include placing a push mechanism, such as the push mechanism 130, in a base 110 of a tissue repair device 100. The push mechanism 130 may include multiple teeth 135 along its length that are engageable with a hook 115 of a keeper 114 coupled to the base 110 such that the push mechanism 130 may be moved distally relative to the base 110. However, movement of the push mechanism 130 of the method may be limited proximally relative to the base 110 by engagement of the hook 115 with each tooth 135 of the push mechanism 130. The teeth 135 of the push mechanism 130 may also be engageable with a driver 125 of an linear actuator 120 that is slideably coupled to the base 110 to move the push mechanism 130 distally when the linear actuator 120 is moved distally relative to the base 110. However, the driver 125 may be configured to disengage from the teeth 135 to allow proximal movement of the linear actuator 120 relative to the push mechanism 130 when the when the linear actuator 120 moves proximally relative to the base 110.

The method of preparing a tissue repair system to selectively deploy multiple implant sets may additionally include connecting two or more pairs of implants, such as the implants 200 1200, for anchoring sutures, such as the sutures 301, 302, 303, with at least one suture 301, 302, 303 per pair of implants 200, 1200. In some embodiments, connecting two or more pairs of implants 200, 1200 for anchoring sutures 301, 302, 303 with at least one suture per pair of implants includes connecting one or more pairs of implants with a suture that passes through each of the implants in the respective one or more pairs to form a suture loop. Connecting two or more pairs of implants 200, 1200 for anchoring sutures 301, 302, 303 with at least one suture per pair of implants may also include connecting one or more pairs of implants such that pulling on each respective suture free end closes a distance between implants of each respective implant pair.

The method may also include placing the two or more pairs of implants 200, 1200 in a needle 150 capable of penetrating tissue. This may include placing one or more implants keyed to a cross-sectionally asymmetrical needle such that rotation of the one or more implants is restricted within the needle. As used herein, a cross-sectionally asymmetrical needle includes a needle with a portion of material removed, even if otherwise symmetrical. Implants keyed to a cross-sectionally asymmetrical needle may include placing one or more implants in a needle, such as the needle 150, with a slit, such as the slit 159 (FIG. 9), along at least a portion of its length. Other embodiments may include, by way of non-limiting example, a protrusion from an inside surface of a wall of a needle that is configured to interface with an implant that has a notch along its length. Placing the two or more pairs of implants 200, 1200 in a needle 150 capable of penetrating tissue may include placing one or more implants 200, 1200 with a diameter that fits substantially within an outside diameter of the needle 150 when the one or more implants 200, 1200 are placed in the needle 150. As illustrated in FIG. 9, the implants 200 fit substantially within the outside diameter of the needle 150, as used herein, because the extents of the implants 200 do not extend substantially beyond the outside diameter of the needle 150. A similar relationship is observable with the implants 1200 and the needle 150 illustrated in FIG. 22. In some embodiments, placing the two or more pairs of implants 200, 1200 in a needle 150 cable of penetrating tissue may include extending each of the at least one sutures 301, 302, 303 (FIGS. 21 and 22) per pair of implants 200, 1200 away from the needle 150 and proximally. Extending each of the at least one sutures per pair of implants away from the needle and proximally may include inserting each of the at least one sutures per pair in a suture management member, such as the suture management member 170 (FIGS. 2, 8, 9, 14, 17, 19, and 21). Some methods may additionally include inserting each of the at least one sutures per pair in a separate area, such as the slots 173 of the suture management member 170. Insertion of the sutures 301, 302, 303 in the slots 173 is illustrated, for example, in FIGS. 1 and 14.

Various embodiments of a system wholly or its components individually may be made from any biocompatible material. Instruments that will not be implanted and remain in a patient may not necessarily be biocompatible. For example and without limitation, materials may include in whole or in part: non-reinforced polymers, reinforced polymers, metals, ceramics, adhesives, reinforced adhesives, and combinations of these materials. Reinforcing of polymers may be accomplished with carbon, metal, or glass or any other effective material. Examples of biocompatible polymer materials include polyamide base resins, polyethylene, Ultra High Molecular Weight (UHMW) polyethylene, low density polyethylene, polymethylmethacrylate (PMMA), polyetheretherketone (PEEK), polyetherketoneketone (PEKK), a polymeric hydroxyethylmethacrylate (PHEMA), and polyurethane, any of which may be reinforced. Example biocompatible metals include stainless steel and other steel alloys, cobalt chrome alloys, zirconium, oxidized zirconium, tantalum, titanium, titanium alloys, titanium-nickel alloys such as Nitinol, and other superelastic or shape-memory metal alloys. Sutures or other similar components of the invention may be single strand, woven, braided, or any combination thereof from any of these or other biocompatible materials. The sutures or other similar components may be any effective natural or synthetic material and may be a use or combination of materials well-known in the art. Sutures or other similar components of various embodiments may be resorbable or not resorbable.

Terms such as proximal, distal, closer, farther, under, and the like have been used relatively herein. However, such terms are not limited to specific coordinate orientations, distances, or sizes, but are used to describe relative positions referencing particular embodiments. Such terms are not generally limiting to the scope of the claims made herein. Any embodiment or feature of any section, portion, or any other component shown or particularly described in relation to various embodiments of similar sections, portions, or components herein may be interchangeably applied to any other similar embodiment or feature shown or described herein.

While embodiments of the invention have been illustrated and described in detail in the disclosure, the disclosure is to be considered as illustrative and not restrictive in character. All changes and modifications that come within the spirit of the invention are to be considered within the scope of the disclosure.

What is claimed is:

1. A method of suturing tissue comprising:
    measuring the tissue to be sutured at a first location and setting a first depth for a needle of a tissue repair device to penetrate the tissue based on a first measurement, the tissue repair device comprising:
        a cylindrical base with a proximal end, a distal end, and a longitudinal axis extending between the proximal and distal ends;
        an actuator disposed about and movable relative to the base along the longitudinal axis of the base;
        a push mechanism extending through the base, the push mechanism selectively engageable with the actuator to be moved distally by the actuator relative to the base;
        the needle coupled to the distal end of the base and through which a distal portion of push mechanism moves distally when the push mechanism is moved distally relative to the base;
        a spring disposed about the base between the base and the actuator, the spring configured to bias the actuator proximally relative to the base; and
        a keeper defined by a u-shaped slot in an annular outer surface of the base, such that the keeper has an annular outer surface and a hook portion extending into an interior of the base, the keeper configured to allow distal movement of the push mechanism relative to the base but to limit proximal movement of the push mechanism relative to the base;
    inserting the needle through the tissue to be sutured;
    moving the actuator distally relative to the base to engage the push mechanism, the push mechanism configured to move a first implant coupled to a first suture out of a distal end of the needle;
    allowing the actuator to move proximally relative to the base, thereby moving the actuator proximally relative to the push mechanism such that the push mechanism is in position to move a second implant from the tissue repair device when the actuator is moved distally again; and using the first implant coupled to the first suture to repair the tissue.

2. The method of claim 1, wherein measuring the tissue to be sutured at the first location includes observing indicia on the needle.

3. The method of claim 1, wherein setting the first depth for the needle of the tissue repair device to penetrate the tissue based on the first measurement includes setting a depth tube relative to the needle.

4. The method of claim 1, wherein moving the actuator includes moving the actuator linearly.

5. The method of claim 1, wherein moving the actuator includes moving the actuator against the spring bias between the base and the actuator.

6. The method of claim 1, wherein moving the actuator distally relative to the base to engage the push mechanism includes engaging teeth of the push mechanism with the hook portion of the keeper.

7. The method of claim 1, wherein moving the actuator distally relative to the base causes the keeper to be pushed laterally.

8. The method of claim 1, wherein moving the actuator distally relative to the base causes the push mechanism to push against the first and second implants and to move the first and second implants distally relative to the needle to move the first implant out of the distal end of the needle.

9. The method of claim 1, wherein allowing the actuator to move proximally relative to the base includes allowing the spring bias between the actuator and the base to move the actuator proximally.

10. The method of claim 1, wherein allowing the actuator to move proximally relative to the base includes pushing the actuator proximally relative to the base.

11. The method of claim 1, wherein allowing the actuator to move proximally relative to the base causes a driver of the actuator to flex laterally to disengage from the push mechanism.

12. The method of claim 11 wherein, when the driver of the actuator is flexing laterally to disengage from the push mechanism, the keeper is engaged with the push mechanism to prevent the push mechanism from moving proximally relative to the needle.

13. The method of claim 1, further comprising:
measuring the tissue to be sutured at a second location and setting a second depth for the needle of the tissue repair device to penetrate the tissue based on a second measurement;
inserting the needle through the tissue to be sutured;
moving the actuator of the tissue repair device distally relative to the base to engage the push mechanism, the push mechanism configured to move the second implant coupled to the first suture out of the distal end of the needle;
allowing the actuator to move proximally relative to the base, thereby moving the actuator proximally relative to the push mechanism such that the push mechanism is in position to move a third implant from the tissue repair device when the actuator is moved distally again; and
using the second implant coupled to the first suture to repair the tissue.

14. The method of claim 13, wherein measuring the tissue to be sutured at the second location includes observing indicia on the needle.

15. The method of claim 13, wherein setting the second depth for the needle of the tissue repair device to penetrate the tissue based on the second measurement includes setting a depth tube relative to the needle.

16. The method of claim 13, wherein moving the actuator includes moving the actuator linearly.

17. The method of claim 13, wherein moving the actuator includes moving the actuator against the spring bias between the base and the actuator.

18. The method of claim 13, wherein moving the actuator distally relative to the base to engage the push mechanism includes engaging teeth of the push mechanism with the hook portion of the keeper.

19. The method of claim 13, wherein moving the actuator of the tissue repair device distally relative to the base causes the keeper to be pushed laterally.

20. The method of claim 13, wherein moving the actuator distally relative to the base causes the push mechanism to push against the second and third implants to move the second and third implants distally relative to the needle to move the second implant out of the distal end of the needle.

21. The method of claim 13, wherein allowing the actuator to move proximally relative to the base includes allowing the spring bias between the actuator and the base to move the actuator proximally.

22. The method of claim 13, wherein allowing the actuator to move proximally relative to the base includes pushing the actuator proximally relative to the base.

23. The method of claim 13, wherein allowing the actuator to move proximally relative to the base causes a driver of the actuator to flex laterally to disengage from the push mechanism.

24. The method of claim 23, wherein, when the driver of the actuator is flexing laterally to disengage from the push mechanism, the keeper is engaged with the push mechanism to prevent the push mechanism from moving proximally relative to the needle.

25. The method of claim 23, further comprising pulling a free end of one or both of the first suture and a second suture to tighten a loop or a length of the first and/or second sutures.

* * * * *